United States Patent [19]

Truman

[11] 3,983,875
[45] Oct. 5, 1976

[54] TAMPON-INSERTER STICK COMBINATION WITH A MODIFIED STICK-RECEIVING SOCKET

[75] Inventor: Charles L. Truman, Hendersonville, N.C.

[73] Assignee: Kimberly-Clark Corporation, Neenah, Wis.

[22] Filed: Feb. 5, 1976

[21] Appl. No.: 655,437

[52] U.S. Cl. .............................. 128/285; 128/270; 128/269
[51] Int. Cl.² ........................................ A61F 13/20
[58] Field of Search .......... 128/270, 285, 2 W, 267, 128/269, 263

[56] References Cited
UNITED STATES PATENTS

| | | | |
|---|---|---|---|
| 3,228,398 | 1/1966 | Leonard et al. | 128/269 |
| 3,255,494 | 6/1966 | Bloch et al. | 128/269 X |
| 3,481,335 | 12/1969 | Beutlich | 128/270 |
| 3,805,786 | 4/1974 | Bernardin et al. | 128/263 |
| 3,863,636 | 2/1975 | Johnson | 128/285 |

Primary Examiner—Aldrich F. Medbery
Attorney, Agent, or Firm—Daniel J. Hanlon, Jr.; William D. Herrick; Raymond J. Miller

[57] ABSTRACT

An improved tampon-inserter stick combination in which the socket disposed in the rear portion of a compressed tampon and adapted to frictionally receive a removable inserter stick is provided with a convex bumper at the base of the socket. The bumper acts as a stop to control the depth to which the leading end of the stick can be pushed into the socket and, by eliminating or minimizing the tapered configuration at the base as found in prior art sockets, assures that the frictional resistance between inserter stick and socket is substantially uniform for all products, while eliminating the possibility that the inserter stick might be pushed too far into the socket during packing, handling or insertion and make removal difficult. The improved socket structure thus insures easy removal of the inserter stick after the tampon has been positioned in the vagina by the user. A tool for forming the socket is also defined.

5 Claims, 8 Drawing Figures

TAMPON-INSERTER STICK COMBINATION WITH A MODIFIED STICK-RECEIVING SOCKET

BACKGROUND OF THE INVENTION

Among the internally applied catamenial tampons presently on the market there is one type which comprises a compressed round-nosed tampon having an inserter stick or elongate rod-like member removably seated and frictionally held in a socket disposed in the rear portion of the tampon. When such a tampon is inserted into the vagina by the user, the greater resistance to movement between the outer surface of the tampon and the vaginal walls as compared to the resistance to movement between the inserter stick and socket walls is relied on to permit withdrawal of the inserter stick from the tampon after insertion. If the stick/socket resistance is higher than the tampon/wall resistance there may be some tendency for the tampon to be moved backward from its insertion depth as the inserter stick is being removed after the tampon has been inserted. In most instances, this latter condition is undesirable and the present invention is designed to provide a socket structure which insures that the frictional resistance between socket and inserter stick will be uniformly low, and will be maintained at a low level by preventing the inserter stick from penetrating too deeply into the socket as external forces are applied during manufacture or insertion.

SUMMARY OF THE INVENTION

In this invention there is provided a conventional compressed tampon, preferably round-nosed and sufficiently compressed to be self-sustaining in its compressed form; a withdrawal string attached near the rear end of the tampon; a longitudinally disposed stick-receiving socket provided in the rear portion of the tampon; and an inserter means comprising a stick or other rod-like member frictionally and removably seated in the socket. The improvement comprises providing a convex bumper at the base of the socket against which the leading end of the inserter stick bears. The bumper at the base of the socket acts as a stop for the stick, and prevents the stick from being too tightly held by the socket walls and thereby minimizes the removal force needed for withdrawal of the stick after insertion of the tampon.

DETAILED DESCRIPTION OF THE PREFERRED EMBODIMENTS

Figure 1:
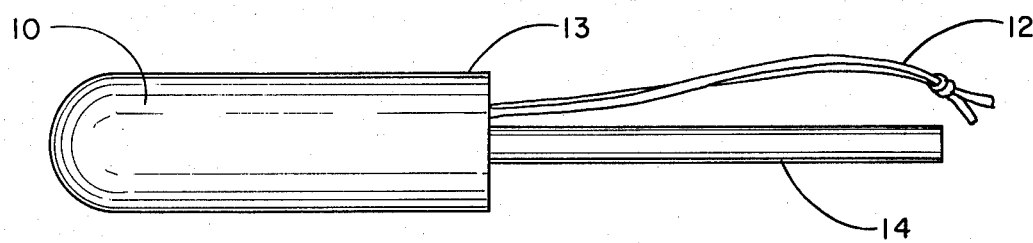
FIG. 1 is a side view of a tampon-inserter stick combination typical of the type of arrangement to which this invention is applicable.

As shown in FIG. 1 of the drawings, the type of tampon combination to which this invention generally applies comprises (a) a compressed round-nosed tampon 10 of absorbent material, (b) a withdrawal string 12 attached to the rear end 13 of the tampon, and (c) an inserter stick 14 removably associated with a stick-receiving socket formed in the rear end portion of the tampon.

The method and apparatus for forming the conventional stick-receiving socket are both well-known in the art and are described in detail in U.S. Pat. No. 3,131,435 under the section entitled "Stick Hole Forming" which may be referred to for information as to the complete details. However for purposes of this invention, prior art FIGS. 2 – 4 are believed sufficient to illustrate that portion of the prior art necessary to understand the improvements provided by this invention.

Figure 2:
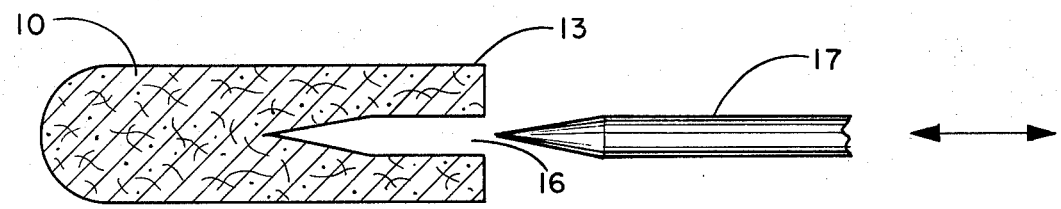
FIG. 2 – 3 are longitudinal sections of a compressed tampon and socket-forming means illustrating the prior art method of spiking and forming the stick-receiving socket in the rear portion of a tampon.

As shown in FIG. 2 a pointed cavity 16 is first formed in the rear end 13 of compressed tampon 10 by driving a sharply pointed forming tool or spike 17 into rear end 13. Spike 17 is adapted for reciprocal movement as indicated by the double ended arrow.

Figure 3:
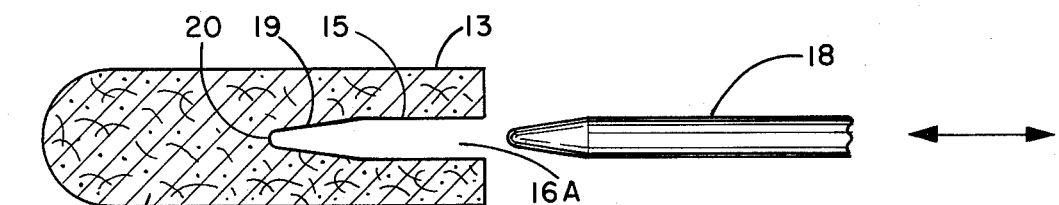

After the initial cavity is formed in the tampon, spike 17 is withdrawn and the tampon is moved to another station where, as shown in FIG. 3 a second forming tool 18 with a tapered end and rounded nose is driven into the preformed cavity to reshape the cavity 16 into its finished configuration in the form of a stick-receiving socket. As illustrated the prior art socket has generally parallel walls 15 which taper at 19 near the base and ends with a concave bottom 20.

Figure 4:
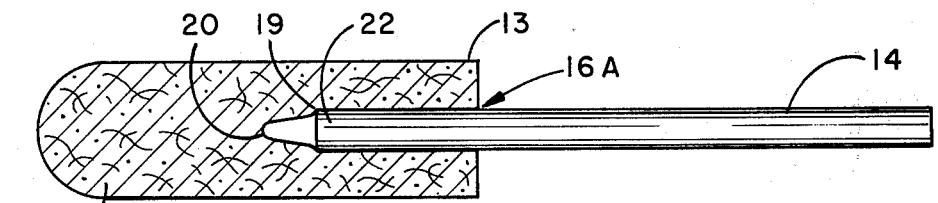
FIG. 4 is a longitudinal section of a tampon similar to FIGS. 2 and 3 illustrating the association of an inserter-stick and the prior art socket.

When the tampon and inserter stick are assembled as shown in FIG. 4 the leading end 22 of inserter stick 14 is frictionally held by walls 19 because the inside diameter of the socket is slightly less than the diameter of the stick. Due to the existence of a short tapered portion of the walls 19 and concave bottom 20 at the base of the socket in the prior art arrangement, it will be noted that the deeper the stick 14 is thrust into socket 16a the stronger is the grip or frictional resistance between tapered walls 19 at the bottom of the socket and leading end 22 of the stick. On some occasions, either during manufacture or use, the depth of penetration of stick 14 into socket 16a is sometimes so deep as to cause the frictional resistance to movement between stick 14 and tapered walls 19 to become undesirably high so that it is difficult to remove the stick after insertion without displacing the tampon from its desired position in the vagina.

Figure 5:
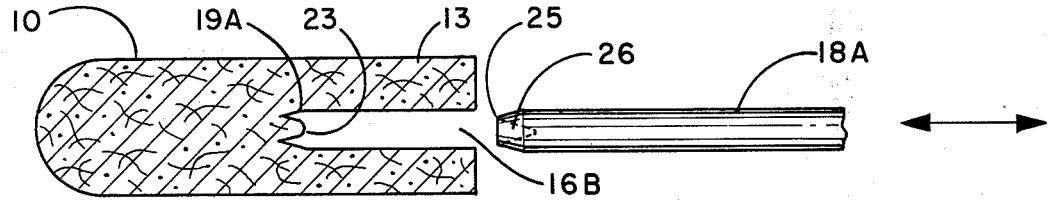
FIG. 5 is a longitudinal section similar to FIG. 3 illustrating the method of forming the improved stick-receiving socket of this invention.
Figure 6:
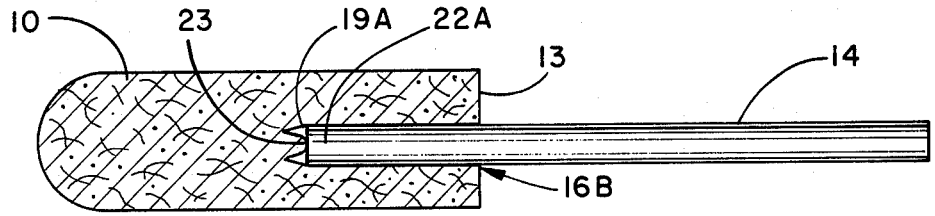
FIG. 6 is a longitudinal section of a tampon showing the association of an inserter stick and the improved socket of this invention.

The present invention overcomes this problem by altering the structure of the stick-receiving socket in a manner which prevents excessive penetration of the stick, into the socket during handling, while still retaining sufficient frictional engagement between stick and socket to maintain the stick in operative, easily removable association with the tampon. This is accomplished by using a modified forming tool, as shown in FIG. 5 and in enlarged detail in FIGS. 7 and 8, to shape the stick-receiving socket after initial spiking. The resulting socket configuration restricts the depth to which the inserter stick can be forced into the socket by providing a convex bumper 23 as a stop at the base of the socket while also minimizing the terminal taper which otherwise results at the base of the socket. As illustrated in these figures, reciprocating forming tool 18a is provided with a tapered forward end in the shape of a short truncated cone with a hollowed out, cup-like leading end 26. The circumference of the leading edge 25 of the truncated cone, or the rim 25 of the cup 26, is a sharp, knifelike member.

When tool 18a is driven into preformed cavity 16, after initial spiking, to shape it into its final configuration, excess fibers are cut away from the walls of the cavity by sharp edges 25 and formed into a firm bumper 23 at the base of socket 16b by the tool's cuplike leading end 26. The height of the bumper may be controlled as desired by varying the depth of the cup-shaped cavity in the tool.

With the improved socket configuration, when the leading edge 22a of inserter stick 14 is pushed into operative association with socket 16b the stick is stopped from being forced too far into socket 16b because of the bumper 23. Frictional resistance between leading end 22a and the walls 19a of socket 16b is thereby controlled to such an extent that there is a minimum amount of variability in the frictional resistance factor between stick and socket in the products so obtained. With this improved structure therefore, a uniform frictional association between stick and tampon is obtained, eliminating one of the major problems of the prior art products.

Figure 7:
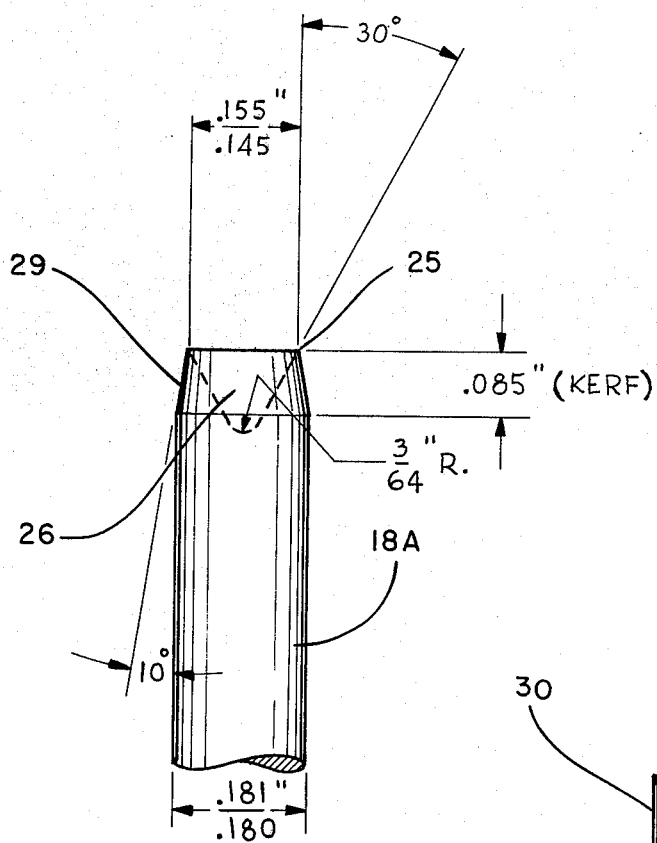
FIG. 7 is an enlarged side view illustrating a preferred forming tool suitable for shaping and sizing the improved socket.
Figure 8:
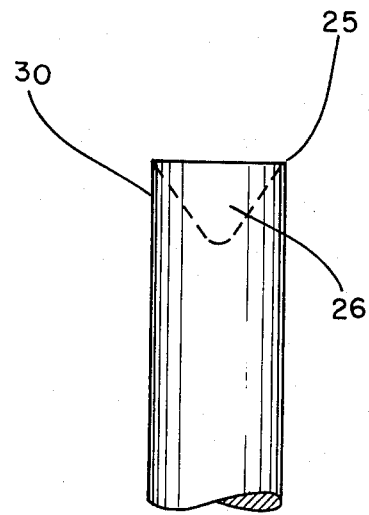
FIG. 8 is an enlarged side view illustrating another embodiment of a suitable forming tool.

As shown in FIG. 7, a preferred forming tool may be a cylindrical rod with a diameter of about 0.180 inch. As indicated in the drawing, the leading end portion 29 of the tool has a 10° taper and an 0.085 inch kerf. The sharpened edge 25 has a diameter of about between about 0.145 inch to 0.155 inch. The cup-shaped cavity has walls with a 30° taper and a concave center with a 3/64 inch radius. After the socket is formed and the tool withdrawn the internal diameter of the formed socket shrinks slightly and will frictionally engage a stick of about 0.156 inch diameter. Proportionate dimensions are easily adapted to accommodate sticks of larger or smaller diameter depending upon the size chosen. In FIG. 8 a modified embodiment of a suitable forming tool is illustrated in which the forward end 30 is not tapered.

The cross-sectional configuration of socket and cooperating inserter stick may also be elliptical, oval, or some shape other than circular. The important consideration, no matter what cross-sectional configuration is chosen, is to minimize taper and to provide a convex bumper at the base of the socket to prevent excess penetration of the inserter stick during manufacture and subsequent handling.

What is claimed is:

1. In a tampon-inserter stick combination which comprises an elongate compressed tampon, a withdrawal string attached to the rear portion of the tampon, a longitudinally disposed stick-receiving socket in the rear portion of the tampon, and an inserter stick removably seated in said socket and frictionally held by the socket walls, the improvement wherein the walls of said socket are substantially parallel and the base of said socket comprises a convex bumper.

2. The improved combination of claim 1 wherein said tampon is round-nosed.

3. The improved combination of claim 1 wherein the cross-sectional configuration of the socket and of the inserter stick is round.

4. The improved combination of claim 1 wherein the cross-sectional configuration of the socket and of the inserter stick is oval.

5. The improved combination of claim 1 wherein the cross-sectional configuration of the socket and of the inserter stick is elliptical.

* * * * *